United States Patent [19]

Kelly

[11] Patent Number: 5,675,037
[45] Date of Patent: Oct. 7, 1997

[54] SELECTIVE ACYLATION OF HYDRAZINES

[75] Inventor: Martha J. Kelly, Norristown, Pa.

[73] Assignee: Rohm and Haas Company, Philadelphia, Pa.

[21] Appl. No.: 628,770

[22] Filed: Dec. 17, 1990

[51] Int. Cl.$^6$ .................................................. C07C 243/10
[52] U.S. Cl. ........................... 564/149; 564/148; 564/150
[58] Field of Search ......................... 564/150, 149, 564/148; 574/614

[56] References Cited

U.S. PATENT DOCUMENTS 4,046,775  9/1977  Bailey ........................ 548/537

FOREIGN PATENT DOCUMENTS 565341   10/1958   Canada.
638995   3/1962    Canada.
0347216  12/1989   European Pat. Off..

OTHER PUBLICATIONS

Synthetic Communications, 17 (14), 1741–1748 (1987).
Chem Abstracts:104:168473w, 1986.

*Primary Examiner*—Shailendra Kumar
*Attorney, Agent, or Firm*—Thomas D. Rogerson

[57] ABSTRACT

This application relates to a process for selectively monoacylating hydrazines by reacting unsubstituted or monoalkylhydrazines with trichloromethyl aryl ketones.

1 Claim, No Drawings

SELECTIVE ACYLATION OF HYDRAZINES

This invention relates to a process for preparing monoacylated hydrazines. More particularly, this invention relates to a process which comprises reacting a trichloromethyl aryl ketone with hydrazine or monoalkylated hydrazine to obtain a monoacyl hydrazine or monoacyl-monoalkylhydrazine. The monoacyl hydrazines and monoacyl-monoalkylhydrazines are useful intermediates in the process of preparing 1-alkyl-1,2-diacylhydrazines which are known to have insecticidal activity against Coleoptera and Lepidoptera.

Selectivity is a problem when acylating hydrazines since hydrazine is a difunctional molecule. There are two types of selectivity problems. One is the selectivity to monoacylate hydrazine while preventing or minimizing diacylation. The other is control of the regioselectivity of acylation for monosubstituted hydrazines. The process of the present invention provides an efficient method of selectively monoacylating hydrazine and, with monoalkylated hydrazines, causing acylation on the unsubstituted nitrogen.

In the process of the instant invention, the hydrazine, or monoalkylated hydrazine is reacted with a trichloromethyl aryl ketone to obtain the desired monoacylated hydrazine derivative.

The general reaction is shown in Equation I,

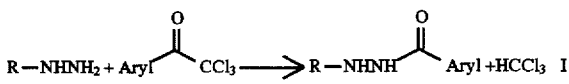

wherein
R is hydrogen or alkyl; and
Aryl is phenyl substituted with one to three substituents independently selected from hydrogen, halo, alkyl, alkoxy, haloalkyl or haloalkoxy; or naphthyl.

Alkyl includes straight or branched alkyl groups, for example ($C_1$–$C_6$)alkyl such as methyl, ethyl, n-propyl, n-butyl, isopropyl, t-butyl, or neopentyl. Alkoxy is, for example ($C_1$–C)alkoxy such as methoxy. Halo means bromo, chloro, fluoro and iodo. Haloalkyl is, for example, halo($C_1$–$C_6$)alkyl such as trifluoromethyl. Haloalkoxy is, for example, halo($C_1$–$C_6$)alkoxy such as trifluoromethoxy.

In a preferred embodiment, R is t-butyl and Aryl is 4-(($C_1$–$C_6$)alkyl)phenyl, 2,3-di($C_1$–$C_6$)alkylphenyl, 4-halophenyl, 2-($C_1$–$C_6$)alkyl-3-($C_1$–$C_6$)alkoxyphenyl, 2-($C_1$–$C_6$)alkyl-3-halophenyl, 2,3-dihalophenyl, 2-halo-3-($C_1$–$C_6$)alkylphenyl, 2,3-di($C_1$–$C_6$)alkoxyphenyl, 2-halo-3-($C_1$–$C_6$)alkoxyphenyl or 2,3,5-tri($C_1$–$C_6$)alkylphenyl.

More preferably, Aryl is 4-ethylphenyl, 4-chlorophenyl, 2,3-dimethylphenyl, 2-methyl-3-methoxyphenyl, 4-methylphenyl, 4-n-propylphenyl, 2-methyl-3-chlorophenyl, 2,3-dimethoxyphenyl, 2-methyl-3-bromophenyl, 2-methyl-3-fluorophenyl, 2,3-dichlorophenyl, 2-fluoro-3-chlorophenyl, 2,3-difluorophenyl, 4-isopropylphenyl, 2-chloro-3-methylphenyl, 2-bromo-3-methylphenyl, 2-chloro-3-methoxyphenyl, 2-ethyl-3-chlorophenyl, 2-fluoro-3-methylphenyl or 2,3-dimethyl-5-isopropylphenyl.

The hydrazine used in the process can be a hydrate such as hydrazine hydrate, the neat hydrazine such as methylhydrazine or a hydrazine salt such as t-butylhydrazine hydrochloride. Other salts include hydrazine sulfate or a hydrazine hydrohalide such as hydrazine hydrochloride. In the case where a hydrazine salt is used, an equivalent of base is added to the reaction to produce the free hydrazine. Examples of bases include potassium carbonate, sodium acetate, sodium methoxide, sodium ethoxide, triethylamine, and sodium hydroxide. The preferred base is sodium hydroxide.

The reaction process is carried out in a variety of solvents such as methanol, ethanol, isopropanol, xylene, water, ethyl acetate, toluene and methylene chloride. Preferred solvents are aprotic solvents such as xylene, toluene and methylene chloride.

The reaction process is carried out preferably at atmospheric pressure.

The process is carried out between about 10° C. and about 100° C., preferably between about 20° C. and about 50° C.

The following examples further illustrate the invention but are not intended to limit it in any way.

EXAMPLES

Example 1

1-(4-Ethylbenzoyl)-2-t-butylhydrazine

To a mixture of t-butylhydrazine hydrochloride (6.36 grams (g), 50 millimoles (mmol)) 5.3 g of water, 20 milliliters (ml) of methylene chloride and 4.0 g of 50% sodium hydroxide solution (50 mmol) under nitrogen there was added dropwise at room temperature over 12 minutes α,α,α-trichloro-4-ethylacetophenone (13.88 g, 95.2% purity, 52.5 mmol). The reaction mixture was stirred at room temperature for 5.75 hours, then 0.4 g of additional sodium hydroxide solution was added and the reaction mixture was stirred overnight. The reaction was quenched with water and the phases were separated. The methylene chloride phase was washed twice with water, dried over magnesium sulfate, filtered and evaporated in vacuo to yield 10.24 g (93% yield) of a pale yellow solid. This was found to contain 92.5% of 1-(4-ethyl)benzoyl-2-t-butylhydrazine, less than 0.3% of the isomer 1-(4-ethyl)benzoyl-1-t-butylhydrazine, and less than 0.3% of the 1,2-di-(4-ethyl)benzoyl-1-t-butylhydrazine.

Example 2

1-(4-Chlorobenzoyl)-2-methylhydrazine

To a mixture of methylhydrazine (1.63 g, 34.6 mmol) and 55 ml of toluene under nitrogen, α,α,α,trichloro-4-chloroacetophenone (8.55 g, 97.9% purity, 34.6 mmol) was added dropwise and the reaction mixture was stirred at room temperature for 2.75 hours. The resulting slurry was filtered and the solids were washed with toluene and dried to yield 3.82 g (70% yield) of 1-(4-chlorobenzoyl)-2-methylhydrazine, mp 129.5°–131° C. (literature mp 132°–133° C., Meyer, R. F., J. Heterocyclic Chem., 1965, 2, 305).

Using essentially the reaction conditions described in Examples 1 and 2 the compounds listed in Table I were prepared. Where reaction conditions differed, they are noted in the Table. The products of the reactions listed in this Table were isolated either by filtering from the reaction solvent, or by extraction into acid, followed by neutralization and extraction of the product from the aqueous phase. The reported melting points are for the isolated material which had not been further purified by recrystallization.

TABLE I

| Ex. No. | Aryl | R | Solvent Temp. | Product Isolation | Yield | mp (°C.) | lit mp (°C.) |
|---|---|---|---|---|---|---|---|
| 3. | Phenyl | $CH_3$ | Toluene RT[2] | Extraction | 73 | 79.5–82 | 85–86[1] 86–88[3] |
| 4. | Phenyl | H | Toluene RT | Filtration | 77 | 111.5–112.5 | 112.5[3] |
| 5. | Phenyl | $C(CH_3)_3$ | Toluene 40° C. | Extraction | 75 | 93.5–94.5 | 94–95[4] |
| 6. | 4-Ethyl-phenyl | $CH_3$ | Toluene RT | Extraction | 81 | 65–71 | |
| 7. | 4-Ethyl-phenyl | $C(CH_3)_3$ | Toluene 40° C. | Filtration | 76 | | |

[1] Meyer, R. F., J. Heterocyclic Chem., 1965, 2, 305.
[2] RT = Room Temperature
[3] Smith, P. A. S., "Derivatives of Hydrazine and other Hydronitrogens having N-N bonds", Benjamin/Cummings Publishing Company, Reading, MA, 1983, p 83.
[4] Macleay et al, U.S. Pat. No. 4,008,273.

By using essentially the reaction conditions described in Examples 1 and 2, Examples 8–26, listed in Table II, are prepared.

TABLE II

| Ex. No. | Aryl | R | Solvent Temp. |
|---|---|---|---|
| 8. | Phenyl | $CH_3$ | Xylene RT |
| 9. | 2,3-Dimethyl-phenyl | $C(CH_3)_3$ | Toluene 40° C. |
| 10. | 2-Methyl-3-methoxyphenyl | $C(CH_3)_3$ | Toluene 40° C. |
| 11. | 4-Methylphenyl | $C(CH_3)_3$ | $CH_2Cl_2$/NaOH RT |
| 12. | 4-n-Propylphenyl | $C(CH_3)_3$ | $CH_2Cl_2$/NaOH RT |
| 13. | 2-Methyl-3-chloro-phenyl | $C(CH_3)_3$ | $CH_2Cl_2$/NaOH RT |
| 14. | 2,3-Dimethoxy-phenyl | $C(CH_3)_3$ | $CH_2Cl_2$/NaOH RT |
| 15. | 2-Methyl-3-bromo-phenyl | $C(CH_3)_3$ | $CH_2Cl_2$/NaOH RT |
| 16. | 2-Methyl-3-fluoro-phenyl | $C(CH_3)_3$ | $CH_2Cl_2$/NaOH RT |
| 17. | 2,3-Dichloro-phenyl | $C(CH_3)_3$ | $CH_2Cl_2$/NaOH RT |
| 18. | 2-Fluoro-3-chloro-phenyl | $C(CH_3)_3$ | $CH_2Cl_2$/NaOH RT |
| 19. | 2,3-Difluorophenyl | $C(CH_3)_3$ | Toluene RT |
| 20. | 4-Isopropylphenyl | $C(CH_3)_3$ | Toluene RT |
| 21. | 2-Chloro-3-methyl-phenyl | $C(CH_3)_3$ | Toluene RT |
| 22. | 2-Bromo-3-methyl-phenyl | $C(CH_3)_3$ | Toluene RT |
| 23. | 2-Chloro-3-methoxy-phenyl | $C(CH_3)_3$ | Toluene RT |
| 24. | 2-Ethyl-3-chloro-phenyl | $C(CH_3)_3$ | Toluene RT |
| 25. | 2-Fluoro-3-methyl-phenyl | $C(CH_3)_3$ | Toluene RT |
| 26. | 2,3-Dimethyl-5-isopropylphenyl | $C(CH_3)_3$ | $CH_2Cl_2$/NaOH RT |

It should be understood that the instant specification and examples are set forth by way of illustration and not limitation, and various modifications and changes may be made without departing from the spirit and scope of the present invention as defined by the appended claims.

What is claimed is:

1. A process for preparing a monoacylated hydrazine of the formula

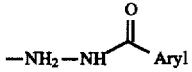

which comprises reacting a hydrazine of the formula

or the corresponding hydrazine hydrate or hydrazine salt with a trichloromethyl aryl ketone of the formula

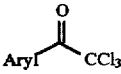

wherein Aryl is phenyl substituted with one to three substituents independently selected from hydrogen, halo, $(C_1-C_6)$alkyl, $(C_1-C_6)$alkoxy, halo$(C_1-C_6)$alkyl or halo$(C_1-C_6)$alkoxy; or naphthyl.

* * * * *